United States Patent
Kennis et al.

(10) Patent No.: US 6,576,640 B1
(45) Date of Patent: Jun. 10, 2003

(54) BENZISOXAZOLES AND PHENONES AS $\alpha_2$-ANTAGONISTS

(75) Inventors: Ludo Edmond Josephine Kennis, Turnhout (BE); Josephus Carolus Mertens, Oud-Turnhout (BE); Serge Maria Aloysius Pieters, Hulst (NL)

(73) Assignee: Janssen Pharmaceutica N.V., Beerse (BE)

( * ) Notice: Subject to any disclaimer, the term of this patent is extended or adjusted under 35 U.S.C. 154(b) by 0 days.

(21) Appl. No.: 09/868,756

(22) PCT Filed: Dec. 14, 1999

(86) PCT No.: PCT/EP99/10054

§ 371 (c)(1),
(2), (4) Date: Jul. 26, 2001

(87) PCT Pub. No.: WO00/37466

PCT Pub. Date: Jun. 29, 2000

(30) Foreign Application Priority Data

Dec. 21, 1998 (EP) .............................. 98204358

(51) Int. Cl.⁷ ................. A61K 31/437; A61K 31/4353; A61K 31/4365; C07D 471/04; C07D 491/048; C07D 495/04; A61P 25/16

(52) U.S. Cl. .......................... 514/291; 546/80; 546/85; 546/89; 514/292

(58) Field of Search .............. 546/80, 85, 89; 514/291, 292

(56) References Cited

U.S. PATENT DOCUMENTS 4,001,263 A * 1/1977 Plattner et al. ............. 260/296

FOREIGN PATENT DOCUMENTS

| EP | 0 178 201 | 4/1986 |
|----|-----------|--------|
| EP | 0 206 225 | 12/1986 |
| EP | 0 339 959 | 11/1989 |
| WO | WO 94/10989 | 5/1994 |
| WO | 98 45297 | 10/1998 |

OTHER PUBLICATIONS

Harbert CA et al J. Med. Chem. (1980) 23, 635–643.*
Montgomery AMJ and Grottick AJ (1999) Pharmacology Biochemistry and Behavior, 62(4), 643–657.*
Nagai et al., Chem Pharm Bull (27(8) 1922–1926 (1979).

* cited by examiner

*Primary Examiner*—Evelyn Mei Huang
(74) *Attorney, Agent, or Firm*—Woodcock Washburn LLP

(57) ABSTRACT

The present invention concerns compounds of formula (I)

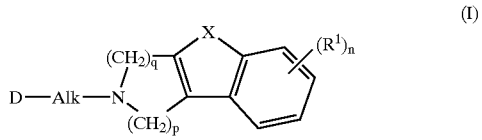

the N-oxide forms, the pharmaceutically acceptable addition salts and the stereochemically isomeric forms thereof, wherein Alk is $C_{5-12}$alkanediyl; n is 1 or 2; p is 1 and q is 2; or p is 2 and q is 1; X is —O—, —S—, —S(=O)—, —S(=O)$_2$— or NR$^2$; each R$^1$ is independently hydrogen, halogen, $C_{1-6}$alkyl, nitro, hydroxy or $C_{1-4}$alkyloxy; R$^2$ is hydrogen, $C_{1-6}$alkyl, aryl or $C_{1-6}$alkyl substituted with aryl; aryl is phenyl or phenyl substituted with a halogen or $C_{1-6}$alkyl; D is an optionally substituted benzophenone or 3-benzisoxazolyl; having central $\alpha_2$-adrenoceptor antagonist activity. It further relates to their preparation, pharmaceutical use and compositions.

7 Claims, No Drawings

BENZISOXAZOLES AND PHENONES AS α₂-ANTAGONISTS

CROSS REFERENCE TO RELATED APPLICATIONS

This application is a National Stage application under 35 U.S.C. §371 of PCT/EP99/10054 filed Dec. 14, 1999, which claims priority from EP 98.204.358.0, filed Dec. 21, 1998.

The present invention concerns benzisoxazoles and phenones having central $\alpha_2$-adrenoceptor antagonist activity. It further relates to their preparation, compositions comprising them and their use as a medicine.

Central $\alpha_2$-adrenoceptor antagonists are known to increase noradrenaline release by blocking presynaptic $\alpha_2$-receptors which exert an inhibiting control over the release of the neurotransmitter. By increasing the noradrenaline concentrations, $\alpha_2$-antagonists can be used clinically for the treatment or prophylaxis of depression, cognitive disturbances, Parkinson's disease, diabetes mellitus, sexual dysfunction and impotence, elevated intraocular pressure, and diseases related to disturbed enterokinesia, since all these conditions are associated with a deficiency of noradrenaline in the central or peripheral nervous system.

WO98/45297, published on Oct. 15, 1998, 1,2,3,4-tetrahydro-benzofuro-[3,2-c]pyridine derivatives having central $\alpha_2$-adrenoceptor antagonist activity.

1-(4-fluorophenyl)-4-(1,3,4,5-tetrahydro-2H-pyrido[4,3-b]indol-2-yl)-1-butanone derivatives are disclosed in Kimura et al. [Arch. Int. Pharmacodyn. Ther. (1971), 190(1), 124–134], Nagai et al. [Chem. Parm. Bull. (1979), 27(8), 1922–1926], Harbert et al. [J. Med. Chem. (1980), 23(6), 635–643 & Mol. Pharmacol. (1980), 17(1), 38–42], Wong et al. [Can. Eur. J. Pharmacol. (1981), 73(2–3), 163–173], Ismaiel et al. [Med. Chem. Res. (1996), 6(3), 197–211], WO 95/07075, WO 94/10989, WO 94/08040, JP 47,029,395, DE 2,514,084, ZA 6,705,178, U.S. Pat. Nos. 3,382,250, 4,001, 263, 4,224,329 and 5,508,306

4-(3,4-dihydrobenzofuro[3,2-c]pyridin-2(1H)-yl)-1-(4-fluorophenyl)-1-butanone derivatives are disclosed in Aksanova et al. [Khim. Farm. Zh. (1975), 9(1), 7–9] as central nervous system blocking agents.

The compounds of the present invention are novel and have a specific and selective binding affinity for the different known subtypes of the ($\alpha_2$-adrenoceptors, i.e. the $\alpha_{2A}$, $\alpha_{2B}$ and $\alpha_{2C}$-adrenoceptor. When compared to the closest art compounds, the present compounds unexpectedly show an improvement in dissociation between binding affinity for the $\alpha_{2A}$-adrenoceptor and the dopamine $D_2$ receptor which is particularly useful when treating depression.

The present invention concerns the compounds of formula

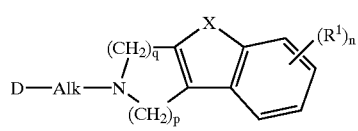

(I)

the N-oxide forms, the pharmaceutically acceptable addition salts and the stereochemically isomeric forms thereof, wherein:

Alk is $C_{5-12}$alkanediyl;
n is 1 or 2;
p is 1 and q is 2; or
p is 2 and q is 1;
X is —O—, —S—, —S(=O)—, —S(=O)$_2$— or NR$^2$;
each R$^1$ is independently hydrogen, halogen, $C_{1-6}$alkyl, nitro, hydroxy or $C_{1-4}$alkyl-oxy;
R$^2$ is hydrogen, $C_{1-6}$alkyl, aryl or $C_{1-6}$alkyl substituted with aryl;
aryl is phenyl or phenyl substituted with a halogen or $C_{1-6}$alkyl;
D is a radical of formula

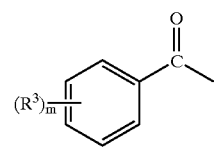

(a)

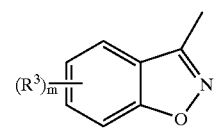

(b)

wherein
m is 1 or 2;
each R$^3$ independently is hydrogen, $C_{1-4}$alkyl, $C_{1-4}$alkyloxy or halo.

As used in the foregoing definitions the term halogen is generic to fluoro, chloro, bromo and iodo. The term $C_{1-4}$alkyl as a group or part of a group defines straight and branched saturated hydro-carbons, having from 1 to 4 carbon atoms such as, for example, methyl, ethyl, propyl, butyl, 1-methylethyl, 1,1-dimethylethyl, 2-methyl-propyl and the like. The term $C_{1-6}$alkyl is meant to include $C_{1-4}$alkyl radicals and the higher homologues thereof having 5 or 6 carbon atoms such as, for example, pentyl, hexyl and the like. The term $C_{6-12}$alkanediyl defines bivalent straight or branch chained alkanediyl radicals having from 5 to 12 carbon atoms such as, for example, 1,6-hexanediyl, 1,7-heptanediyl, 1,8-octanediyl, 1,9-nonanediyl, 1,10-decanediyl, 1,11-undecanediyl, 1,12-dodecanediyl and the like. The term $C_{5-12}$alkanediyl is meant to include $C_{6-12}$alkanediyl and the lower homologue having 5 carbon atoms such as, for example, 1,5-pentanediyl and the like.

The addition salts as mentioned herein are meant to comprise the therapeutically active addition salt forms which the compounds of formula (I) are able to form with appropriate acids, such as, for example, inorganic acids such as hydrohalic acids, e.g. hydrochloric or hydrobromic acid; sulfuric; nitric; phosphoric and the like acids; or organic acids such as, for example, acetic, propanoic, hydroxyacetic, lactic, pyruvic, oxalic, malonic, succinic, maleic, fumaric, malic, tartaric, citric, methanesulfonic, ethanesulfonic, benzenesulfonic, p-toluenesulfonic, cyclamic, salicylic, p-aminosalicylic, pamoic and the like acids.

The pharmaceutically acceptable addition salts as mentioned hereinabove are also meant to comprise the therapeutically active non-toxic base, in particular, a metal or amine addition salt forms which the compounds of formula (I) are able to form. Said salts can conveniently be obtained by treating the compounds of formula (I) containing acidic hydrogen atoms with appropriate organic and inorganic bases such as, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like. Conversely said salt forms can be converted by treatment with an appropriate base or acid into the free acid or base form.

The term addition salt as used hereinabove also comprises the solvates which the compounds of formula (I) are able to form and said solvates are meant to be included within the scope of the present invention. Examples of such solvates are, e.g. the hydrates, alcoholates and the like.

The N-oxide forms of the compounds of formula (I) are meant to comprise those compounds of formula (I) wherein one or several nitrogen atoms are oxidized to the so-called N-oxide.

The term stereochemically isomeric forms as used herein defines all the possible isomeric forms in which the compounds of formula (I) may occur. Unless otherwise mentioned or indicated, the chemical designation of compounds denotes the mixture of all possible stereochemically isomeric forms, said mixtures containing all diastereomers and enantiomers of the basic molecular structure.

Some of the compounds of formula (I) may also exist in their tautomeric forms. Such forms although not explicitly indicated in the above formula are intended to be included within the scope of the present invention.

Whenever used hereinafter, the term compounds of formula (I) is meant to include also the N-oxide forms, the pharmaceutically acceptable addition salts and all stereoisomeric forms.

As used hereinafter, when the position of the $R^1$ substituent is referred to, the following numbering is used:

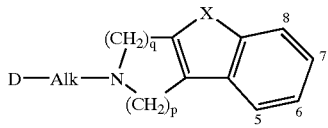

An interesting group of compounds are those compounds of formula (I) wherein n is 1 and $R^1$ is hydrogen, chloro, fluoro, methyl, methoxy or nitro, in particular $R^1$ is hydrogen, chloro or methoxy.

In case $R^1$ is other than hydrogen, then $R^1$ is suitably connected to the tricyclic ring system in the 6 or 7 position.

Another interesting group of compounds are those compounds of formula (I) wherein Alk is 1,5-pentanediyl.

Still another interesting group of compounds are those compounds of formula (I) wherein D is a radical of formula (a) and $R^3$ is fluoro, bromo, methoxy, methyl or hydrogen, in particular, fluoro.

Compounds of formula (I) wherein D is a radical of formula (b) are also of particular interest.

Particular compounds are those compounds of formula (I) wherein X is O, S or NH.

The compounds of formula (I) can generally be prepared by N-alkylating an intermediate of formula (II) with an alkylating reagent of formula (III) following the procedure described in EP-A-0,037,265, EP-A-0,070,053, EP-A-0,196,132 and in EP-A-0,378,255. In particular, the N-alkylation may be performed in a reaction-inert solvent such as, for example, methyl isobutyl keton, N,N-dimethylformamide or N,N-dimethylacetamide, in the presence of a base such as, for example, triethylamine, sodium carbonate or sodiumbicarbonate, and optionally in the presence of a catalyst such as, for example, potassium iodide.

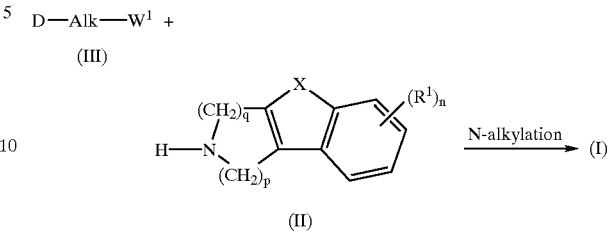

In intermediate (III), $W^1$ represents an appropriate reactive leaving group such as, for example, halo, e.g. chloro, bromo or iodo; sulfonyloxy, e.g. methanesulfonyloxy, 4methylbenzenesulfonyloxy.

In this and the following reactions, the reaction products may be isolated from the reaction medium and, if necessary, further purified according to methodologies generally known in the art such as extraction, crystallization, trituration and chromatography.

The compounds of formula (I) may be converted into each other following art-known functional group transformation reactions.

The compounds of formula (I) may also be converted to the corresponding N-oxide forms following art-known procedures for converting a trivalent nitrogen into its N-oxide form. Said N-oxidation reaction may generally be carried out by reacting the starting material of formula (I) with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarbo-peroxoic acid or halo substituted benzenecarboperoxoic acid, e.g. 3-chlorobenzene-carboperoxoic acid, peroxoalkanoic acids, e.g. peroxoacetic acid, alkylhydroperoxides, e.g. tert-butyl hydroperoxide. Suitable solvents are, for example, water, lower alkanols, e.g. ethanol and the like, hydrocarbons, e.g. toluene, ketones, e.g. 2-butanone, halogenated hydrocarbons, e.g. dichloromethane, and mixtures of such solvents.

A number of intermediates and starting materials are commercially available or are known compounds which may be prepared according to art-known methodologies.

For example, some of the intermediates of formula (III) and their preparations are described in EP-A-0,037,265, EP-A-0,070,053, EP-A-0,196,132 and in EP-A-0,378,255.

Intermediates of formula (II) wherein X is O can be prepared analogous to the procedures described in Cattanach C. et al. (J. Chem. Soc (C), 1971, p53–60); Kartashova T. (Khim. Geterotsikl. Soedin., 1979 (9), p 1178–1180) and Zakusov. V. Et al. (Izobreteniya, 1992 (15), p 247). Intermediates of formula (II) wherein X is S can be prepared analogous to the procedure described in Capps et al (J. Am. Chem. Soc., 1953, p. 697) or U.S. Pat. No. 3,752,820.

A particular synthesis route for the preparation of intermediates of formula (II) wherein p is 1 and q is 2, said intermediates being represented by formula (II-1), is depicted in scheme 1.

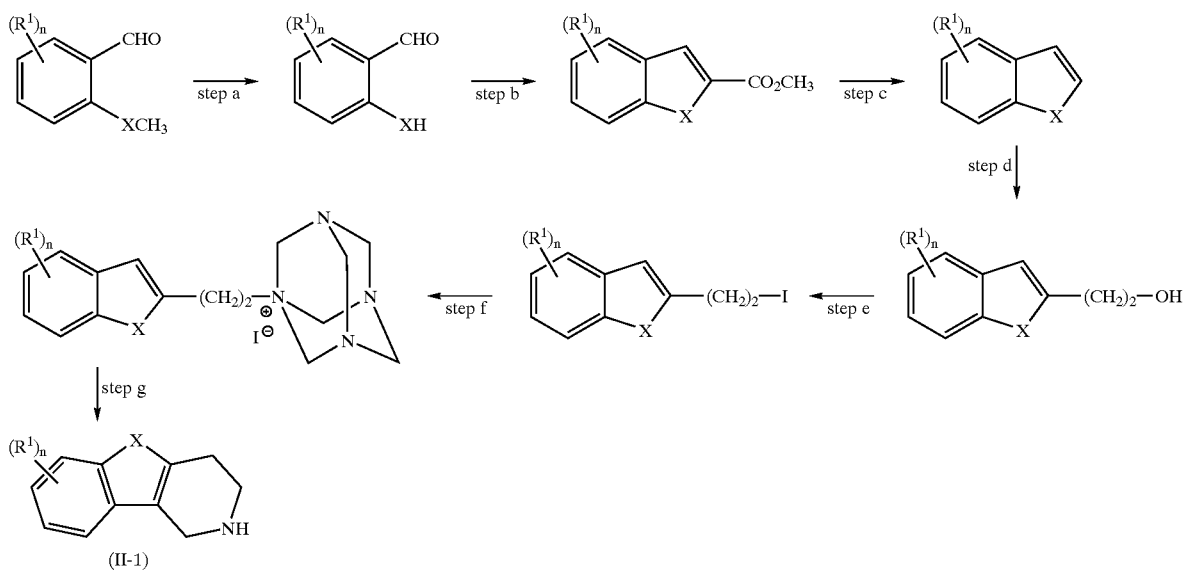

Step a can be performed analogous to the procedure described in Tetrahedron (1981), 37, p 979–982. Benzofurans resulting from step c have been used as intermediates in U.S. Pat. No. 4,210,655. The further reaction steps are analogous to the reaction procedures described in U.S. Pat. No. 3,752,820.

Alternatively, intermediates of formula (II-1) can be prepared using the reaction steps depicted in scheme 2.

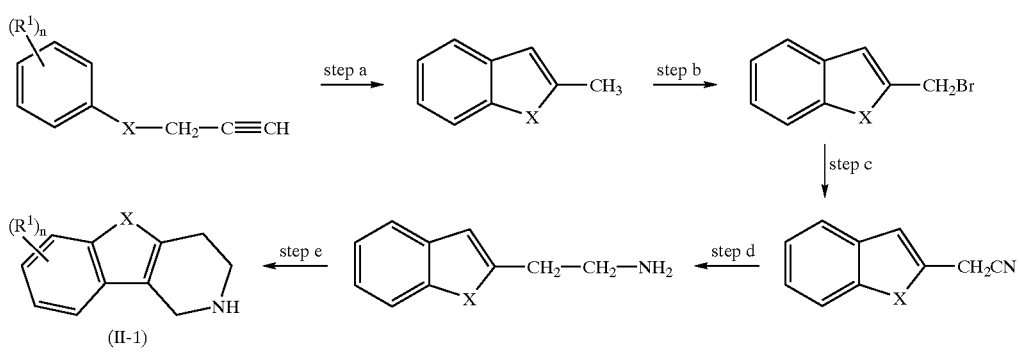

Step a can be performed analogous to the procedure described in Heterocycles (1994), 39(1), p. 371–380. Step b can be performed analogous to the procedure described in J. Med. Chem. (1986), 29(9), p. 1643–1650. Further reaction steps can be performed analogous to the ones described in J. Heterocycl. Chem. (1979), 16, p. 1321.

Intermediates of formula (II) wherein p is 2 and q is 1, said intermediates being represented by formula (II-2), can be prepared according to Synth. Comm., 1995, p3883–3900 and using methods known in the art. A general procedure is depicted in scheme 3.

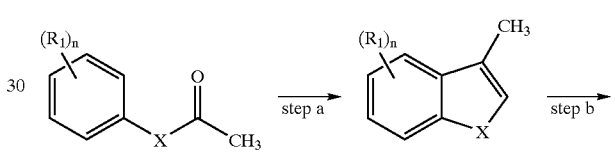

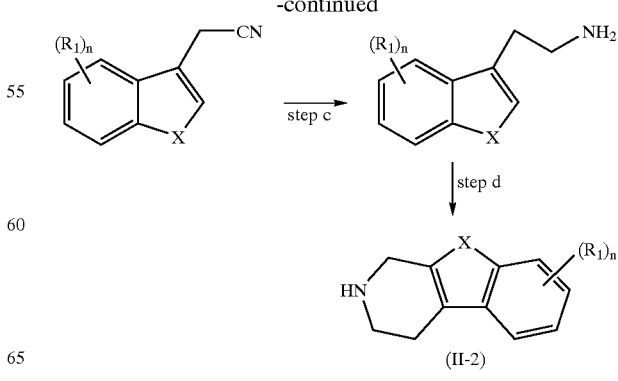

Intermediates of formula (II-2) wherein X is —O—, said intermediates being represented by formula (II-2-a), can be prepared as described in Syn. Comm. (1995), p3883–3900 and J. Chem. Soc., 1965, p4939–4953 and using methods known in the art. A general procedure is depicted in scheme 4.

forms of said compounds and said intermediates can be obtained by the application of art-known procedures. For example, diastereoisomers can be separated by physical methods such as selective crystallization or chromatographic techniques, e.g. counter current distribution, liquid chromatography and the like methods. Enantiomers can be

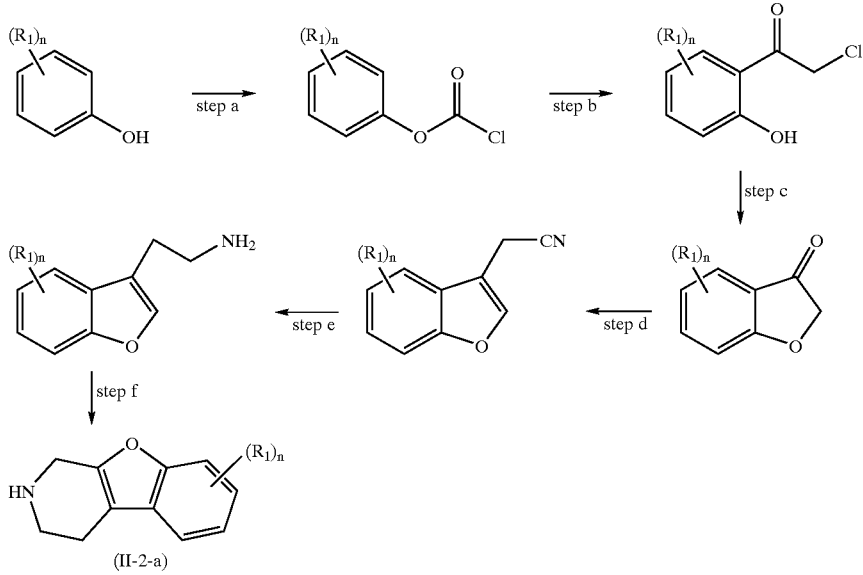

Scheme 4

Intermediates of formula (II-2) wherein X is —S—, said intermediates being represented by formula (II-2-b), can be prepared according to J. Med. Chem., 1992, 35(7), p1176–1182 and using methods known in the art. A general procedure is depicted in scheme 5.

obtained from racemic mixtures by first converting said racemic mixtures with suitable resolving agents such as, for example, chiral acids, to mixtures of diastereomeric salts or compounds; then physically separating said mixtures of diastereomeric salts or compounds by, for example, selective crystallization or chromatographic techniques, e.g. liquid

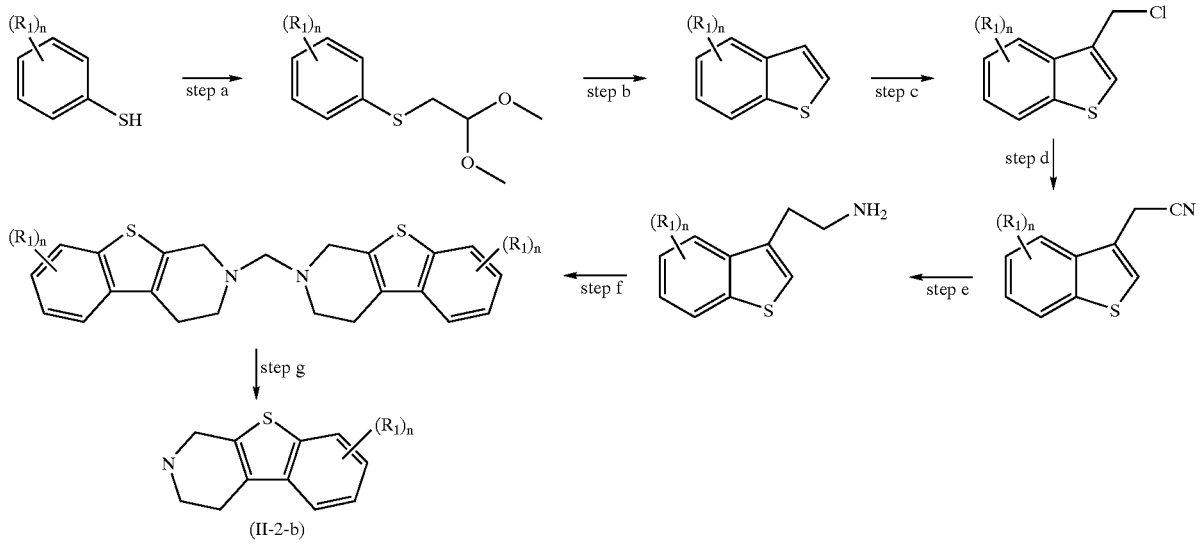

Scheme 5

Some of the compounds of formula (I) and some of the intermediates in the present invention contain at least one asymmetric carbon atom. Pure stereochemically isomeric chromatography and the like methods; and finally converting said separated diastereomeric salts or compounds into the corresponding enantiomers.

Pure stereochemically isomeric forms of the compounds of formula (I) may also be obtained from the pure stereochemically isomeric forms of the appropriate intermediates and starting materials, provided that the intervening reactions occur stereospecifically. The pure and mixed stereochemically isomeric forms of the compounds of formula (I) are intended to be embraced within the scope of the present invention.

The compounds of formula (I), the N-oxides, the pharmaceutically acceptable addition salts and stereochemically isomeric forms thereof, block the presynaptic $\alpha_2$-receptors on central noradrenergic neurons thus increasing the noradrenaline release. Blocking said receptors will suppress or relieve a variety of symptoms associated with a deficiency of noradrenaline in the central or peripheral nervous system. Therapeutic indications for using the present compounds are depression, cognitive disturbances, Parkinson's disease, diabetes mellitus, sexual dysfunction and impotence and elevated intraocular pressure.

In particular, the present compounds show a larger dissociation between binding affinity for $\alpha_2$-receptors and that for dopamine receptors, especially between $\alpha_{2A}$-receptors and dopamine $D_2$ receptors. This larger dissociation reduces the risk of extrapyramidal side effects (EPS) that might arise from dopamine receptor blockade and that should be avoided in the treatment of depression.

Blocking $\alpha_2$ receptors in the central nervous system has also been shown to enhance the release of serotonine which may add to the therapeutic action in depression (Maura et al., 1992, Naunyn-Schmiedeberg's Arch. Pharmacol., 345: 410–416).

It has also been shown that blocking $\alpha_2$ receptors may induce an increase of extracellular DOPAC (3,4-dihydrophenylacetic acid) which is a metabolite of dopamine and noradrenaline.

In view of the usefulness of the subject compounds in the treatment of diseases associated with a deficiency of noradrenaline in the central nervous system, in particular depression and Parkinson's disease, the present invention provides a method of treating warm-blooded animals suffering from such diseases, in particular depression and Parkinson's disease, said method comprising the systemic administration of an therapeutically effective amount of a compound of formula (I) or a pharmaceutically acceptable addition salt thereof.

The present compounds are also potentially useful in the treatment of Alzheimer's disease and dementia as it is known that $\alpha_2$-antagonists promote the release of acetylcholine (Tellez et al. 1997, J. Neurochem. 68:778–785).

In general it is contemplated that an effective therapeutic daily amount would be from about 0.01 mg/kg to about 4 mg/kg body weight.

The present invention thus also relates to compounds of formula (I) as defined hereinabove for use as a medicine. Further, the present invention also relates to the use of a compound of formula (I) for the manufacture of a medicament for treating depression or Parkinson's disease.

Ex vivo as well as in vitro receptor signal-transduction and receptor binding studies can be used to evaluate the $\alpha_2$ adrenoceptor antagonism of the present compounds. As indices of central $a_2$-adrenoceptor blockade in vivo, the reversal of the loss of righting reflex observed in rats after intravenous injection of xylazine and inhibition of the tremors induced by reserpine in rats can be used.

The compounds of the present invention also have the ability to rapidly penetrate into the central nervous system.

For administration purposes, the subject compounds may be formulated into various pharmaceutical compositions comprising a pharmaceutically acceptable carrier and, as active ingredient, a therapeutically effective amount of a compound of formula (I). To prepare the pharmaceutical compositions of this invention, an effective amount of the particular compound, in addition salt or in free acid or base form, as the active ingredient is combined in intimate admixture with a pharmaceutically acceptable carrier, which may take a wide variety of forms depending on the form of preparation desired for administration. These pharmaceutical compositions are desirably in unitary dosage form suitable, preferably, for administration orally, percutaneously, or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable solutions containing compounds of formula (I) may be formulated in an oil for prolonged action. Appropriate oils for this purpose are, for example, peanut oil, sesame oil, cottonseed oil, corn oil, soy bean oil, synthetic glycerol esters of long chain fatty acids and mixtures of these and other oils. Injectable suspensions may also be prepared in which case appropriate liquid carriers, suspending agents and the like may be employed. In the compositions suitable for percutaneous administration, the carrier optionally comprises a penetration enhancing agent and/or a suitable wettable agent, optionally combined with suitable additives of any nature in minor proportions, which additives do not cause any significant deleterious effects on the skin. Said additives may facilitate the administration to the skin and/or may be helpful for preparing the desired compositions. These compositions may be administered in various ways, e.g., as a transdermal patch, as a spot-on or as an ointment. Addition salts of (I) due to their increased water solubility over the corresponding free base or free acid form, are obviously more suitable in the preparation of aqueous compositions.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect, in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

The following examples are intended to illustrate the present invention.

EXPERIMENTAL PART
A. Preparation of the Intermediates

Example A1

A mixture of O-phenylhydroxylamine hydrochloride (1:1) (0.625 mol) and 4,4-piperidinediol hydrochloride (1:1) (0.682 mol) in 2-propanol (615 ml) was stirred at 20° C. HCl (353 ml) was added dropwise at 20° C. The reaction mixture was gently heated to reflux temperature. The reaction mixture was stirred and refluxed for 3 hours, then cooled to room temperature. The precipitate was filtered off, washed with diisopropyl ether, and dried. This fraction was crystallized from water (1600 ml). The desired compound was allowed to crystallize out while stirring. The precipitate was filtered off, washed with 2-propanol and diisopropyl ether, then dried, yielding 84 g (64%) of 1,2,3,4-tetrahydrobenzo-furo[3,2-c]pyridine hydrochloride (1:1)(interm. 1).

Example A2 a) Reaction under $N_2$ atmosphere. NaH 60% (0.17 mol) was stirred in tetrahydrofuran (350 ml). A solution of diethyl (cyanomethyl)phosphonate (0.17 mol) in tetrahydrofuran (150 ml) was added dropwise over ±20 minutes. (exothermic temperature rise to 30° C.). The mixture was stirred for 20 minutes at room temperature, then cooled to 0° C. A solution of 5-methyl-3(2H)-benzofuranone (0.15 mol) in tetrahydrofuran (350 ml) was added dropwise over 30 minutes at 0° C. The reaction mixture was stirred overnight at room temperature, then poured out into water (1500 ml) and stirred. This mixture was extracted with ether, diisopropyl ether (2×), dried, filtered and the solvent was evaporated. The residue was purified by column chromatography over silica gel (eluent: $CH_2Cl_2$/hexane 50/50). The desired fractions were collected and the solvent was evaporated, yielding 21.2 g (82%) of 5-methyl-3-benzofuranacetonitrile (interm. 2).

b) A mixture of intermediate (2) (0.12 mol) in $NH_3$/$CH_3OH$ (400 ml) was hydrogenated with Raney Nickel (3 g) as a catalyst. After uptake of $H_2$ (2 equiv), the catalyst was filtered off and the filtrate was evaporated. The residue was purified over silica gel on a glass filter (eluent: $CH_2Cl_2$ ($CH_3OH$/$NH_3$) 98/2 to 96/4). The desired fractions were collected and the solvent was evaporated. The residue (±2.1 g) was dissolved in 2-propanol (500 ml), and converted into the hydrochloric acid salt (1:1) with $HCl_2$/2-propanol. The mixture was stirred at room temeprature. The solvent was evaporated. The residue was stirred in diisopropyl ether, filtered off and dried, yielding 24.4 g (96%) of 5-methyl-3-benzofuranethanamine hydrochloride (1:1) (interm. 3).

c) A mixture of intermediate (3) (0.0024 mol) in $H_2O$ (2 ml), acetic acid (2 ml) and formol 37% (2 ml) was stirred for one hour at 100° C. The reaction mixture was cooled and poured out into 1 M NaOH (50 ml). The precipitate was filtered off, washed with water, then dissolved in 1 N HCl (100 ml). The mixture was stirred for 15 minutes on a warm-water-bath (80° C.). The solvent was evaporated. 2-Propanol was added. The solvent was evaporated. The residue was stirred in boiling 2-propanone, then allowed to cool to room temperature while stirring. The precipitate was filtered off and dried, yielding 0.40 g of 1,2,3,4-tetrahydro-6-methylbenzofuro[2,3-c]pyridine monohydrochloride.monohydrate (interm. 4).

Example A3 a) Butyl lithium (0.27 mol of a 2.5 M solution) was added dropwise to 6-methoxy-benzo[b]thiophene [prepared analogous to the procedure described in J. Med. Chem. 1989, 32(12), 2548–2554] (0.25 mol) in tetrahydrofuran (1000 ml), stirred at −30° C. The mixture was stirred for 10 minutes at −30° C. Ethylene oxide (0.38 mol in 100 ml tetrahydrofuran) was added dropwise at −30° C. The mixture was allowed to warm to room temperature and stirred for 3 hours. The mixture was acidified with dilute HCl solution. The solvent was evaporated. The residue was diluted with water and this mixture was extracted with $CH_2Cl_2$. The separated organic layer was dried, filtered and the solvent evaporated. The residue was stirred in hexane, filtered off and dried, yielding 41.3 g 6-methoxybenzo[b]thiophene-2-ethanol (interm. 5).

b) Methanesulfonylchloride (0.21 mol) was added to a mixture of intermediate 5 (0.19 mol) and triethylamine (0.21 mol) in $CH_2Cl_2$ (1000 ml), stirred at 0° C. The reaction mixture was stirred for 4 hours at room temperature, then poured out into water. The separated organic layer was dried, filtered and the solvent evaporated. The residue was triturated under diisopropylether, filtered off and dried, yielding 50.5 g (94%) of 6-methoxybenzo[b]thiophene-2-ethanol methanesulfonate (ester) (interm. 6).

c) A mixture of intermediate 6 (0.18 mol) and NaI (0.45 mol) in 2-propanone (1000 ml) was stirred and refluxed for 9 hours, then cooled to room temperature and the solvent was evaporated. The residue was washed with water and extracted with $CH_2Cl_2$. The separated organic layer was dried, filtered and the solvent evaporated, yielding 57 g of 2-(2-iodoethyl)-6-methoxybenzo[b]thiophene (interm. 7).

d) Intermediate 7 (0.18 mol) was added portionwise to a mixture of 1,3,5,7-tetraazatricyclo[5.1.1.13,5]decane (0.45 mol) in $CHCl_3$ (600 ml). The reaction mixture was stirred and refluxed overnight, then cooled to room temperature. The precipitate was filtered off and dried, yielding 54.2 g of 1-[2-(6-methoxybenzo[b]thiophen-2-yl)ethyl]-1,3,5,7-tetraazatricyclo[5.1.1.1 5,7]decanium iodide (interm. 8).

e) A mixture of intermediate 8 (0.12 mol) and HCl (0.50 mol) in ethanol (171 ml) was stirred for 2 days at room temperature. More HCl (10 ml) and ethanol (40 ml) were added and the reaction mixture was stirred and refluxed for one hour, then cooled to room temperature. The solvent was evaporated. The residue was stirred in 2-propanol, then filtered off. The solid was dried and the residue was reconverted into the free base with 20% NaOH. The separated organic layer was dried, filtered and the solvent evaporated. The residue was dissolved in 2-propanol and converted into the hydrochloric acid salt (1:1) with $HCl_2$/2-propanol. The precipitate was filtered off and dried, yielding 13.1 g (50%) of 1,2,3,4-tetrahydro-7-methoxy-[1]benzothieno[3,2-c]pyridine (interm 9).

Analogously, 1,2,3,4-tetrahydro-8-methyl-[1]benzothieno[3,2-c]pyridine hydrochloride (interm. 10) was prepared.

Example A4 a) A mixture of formol (37%; 31 g) and $ZnCl_2$ (10 g) in ethyl acetate (90 ml) and HCl (12 N; 190 ml) was stirred at −10° C. HCl (gas) was allowed to bubble through the mixture until saturation (at −10° C.). 5-Fluoro-benzo[b]thiophene (0.35 mol) was added dropwise at <0° C. The reaction mixture was stirred overnight at room temperature. Toluene (200 ml) was added and the mixture was stirred vigorously. The organic layer was separated, washed with an aqueous $NaHCO_3$ solution and with water, dried, filtered and the solvent was evaporated. The residue was triturated under hexane, filtered off and dried, yielding 58 g (82.6%) of 3-(chloromethyl)-5-fluorobenzo[b]-thiophene (interm 11).

b) A mixture of NaCN (0.33 mol) and dibenzo-18-crown ether (0.050 g) in dimethyl sulfoxide (110 ml) was stirred at 30° C. Intermediate 11 (0.29 mol) was added slowly. The mixture was allowed to cool to room temperature while stirring. Then, the reaction mixture was stirred in ice-water. The precipitate was filtered off, washed with water, then dissolved in $CH_2Cl_2$. The organic solution was dried, filtered and the solvent was evaporated, yielding 5-fluorobenzo[b]thiophene-3-acetonitrile (interm 12).

c) A mixture of intermediate 12 (0.29 mol) in a mixture of $NH_3$ and $CH_3OH$ (700 ml) was hydrogenated at 14° C. with Raney Nickel (5 g) as a catalyst in the presence of a thiophene solution (10 ml). After uptake of $H_2$ (2 equiv), the catalyst was filtered off over dicalite and the filtrate was evaporated. The residue was purified by column chromatography over silica gel (eluent: $CH_2Cl_2/(CH_3OH/NH_3)$ 96/4). The desired fractions were collected and the solvent was evaporated. The residue was dissolved in diisopropyl ether and converted into the hydrochloric acid salt (1:1) with $HCl_2$/2-propanol. The precipitate was filtered off, washed with diisopropyl ether, and dried, yielding 48.5 g 5-fluorobenzo[b]thiophene-3-ethanamine hydrochloride (interm. 13).

d) A mixture of intermediate 13 (0.21 mol) in water (190 ml), acetic acid (190 ml) and formol (37%; 190 ml) was stirred and refluxed for one hour. The mixture was allowed to cool to room temperature, then poured out in NaOH (4 M; 1200 ml), while stirring. The precipitate was filtered off and triturated under $CH_3CN$, filtered off, washed with diisopropyl ether and dried, yielding 21 g 1,1'-methylenebis[6-fluoro-1,2,3,4-tetrahydro-[1]benzothieno[2,3-c]pyridine (intern. 14).

e) A mixture of intermediate 14 (0.049 mol) in water (1700 ml) and HCl (12 N; 285 ml) was stirred and refluxed for one hour. the precipitate was filtered off, washed with $CH_3CN$ and diisopropyl ether, and dried, yielding 17.7 g 6-fluoro-1,2,3,4-tetrahydro-[1]benzothieno[2,3-c]pyridine hydrochloride (interm. 15).

EXAMPLE A5

A mixture of $AlCl_3$ (32 g) in methoxybenzene (250 ml) was stirred at 0° C. 5-Chloro-pentanoyl chloride (0.24 mol) was added dropwise at 0° C. The reaction mixture was stirred for 3 hours at 0 to 5° C. and then allowed to rise to 15° C. The mixture was poured out onto ice water (400 g) and HCl 12N (100 ml), and extracted with $CH_2Cl_2$. The organic layer was separated, dried, filtered over dicalite and the solvent was evaporated. The residue was stirred in petroleum ether and diisopropyl ether, and the resulting oil was separated, yielding 50.4 g 6-chloro-1-(4-methoxyphenyl)-1-hexanone (interm. 16).

EXAMPLE A6 a) Reaction under $N_2$ atmosphere. $BF_3$ in diethylether (215 ml) was cooled to 0° C. 3-Fluoro-phenol (0.25 mol) was added. 6-Chloro-hexanoyl chloride (0.51 mol) added and the resulting reaction mixture was stirred for 15 min at 0° C., then allowed to warm to room temperature. The reaction mixture was then stirred overnight at 130° C. The mixture was cooled room temperature. Water was added while cooling. This mixture was extracted twice with diisopropyl ether. The separated organic layer was dried, filtered and the solvent was evaporated. The residue was by column chromatography over silica gel (eluent: $CH_2Cl_2$/hexane 50/50), then by HPLC (eluent: $CH_2Cl_2$/hexane 50/50). The fractions were collected and the solvent was evaporated, yielding 52.2 g of 6-chloro-1-(4-fluoro-2-hydroxyphenyl)-1-hexanone (interm 17).

b) A mixture of intermediate 17 (0.21 mol) and hydroxylamine hydrochloride (0.25 mol) in pyridine (100 ml) was stirred for 2 days at room temperature, then poured out into 1 N HCl (450 ml). This mixture was stirred for 10 min, then extracted with ethylacetate (2×). The separated organic layer was dried, filtered and the solvent evaporated. The residue was purified by column chromatography over silica gel (eluent: $CH_2Cl_2/CH_3OH$ 99/1). The desired fractions were collected and the solvent was evaporated, yielding 22 g 6-chloro-1-(4-fluoro-2-hydroxyphenyl)-1-hexanone, oxime (interm. 18).

c) Intermediate 18 (0.017 mol) in tetrahydrofuran (50 ml) was warmed to 60° C. A solution of 1,1'-carbonylbis-1H-imidazole (0.035 mol) in tetrahydrofuran (200 ml) was added dropwise and the resulting reaction mixture was stirred and refluxed for 2 hours. The reaction mixture was cooled to room temperature and the solvent was evaporated. The residue was washed with water, then acidified with HCl. This mixture was extracted with $CH_2Cl_2$. The separated organic layer was dried, filtered and the solvent evaporated. The residue was purified by column chromatography over silica gel (eluent: $CH_2Cl_2$ 100%). The desired farctions were collected and the solvent was , yielding 3-(5-chloropentyl)-6-fluoro-1,2-benzisoxazole (interm. 19).

B. Preparation of the Compounds of Formula (I)

Example B1

A mixture of 6-chloro-1-(4-fluorophenyl)-1-hexanone (0.018 mol), intermediate 1 (0.015 mol), $Na_2CO_3$ (4 g) and potassium iodide (catalytic quantity) in methyl isobutyl ketone (200 ml) was stirred and refluxed overnight and then cooled to room temperature. The solvent was evaporated. The residue was washed with $H_2O$ and the mixture was extracted with $CH_2Cl_2$. The organic layer was separated, dried, filtered and the solvent was evaporated. The residue was purified by column chromatography over silica gel (eluent: $CH_2Cl_2/CH_3OH$ 95/5). The pure fractions were collected and the solvent was evaporated. The residue was converted into the (E)-2-butenedioic acid salt (1:1); The precipitate was filtered off and dried, yielding 5.1 g 1-(4-fluorophenyl)-6-(1,2,3,4-tetrahydrobenzofuro[3,2-c]pyridin-2-yl)-1-hexanone (E)-2-butenedioate (1:1) (71%).

Tables 1, 2 and 3 list compounds of formula (I) which were prepared analogously to example B 1.

TABLE 1

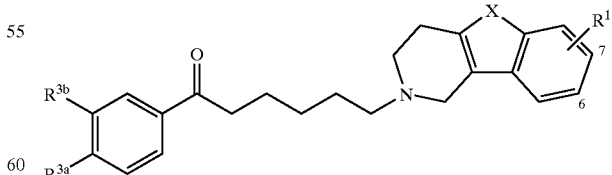

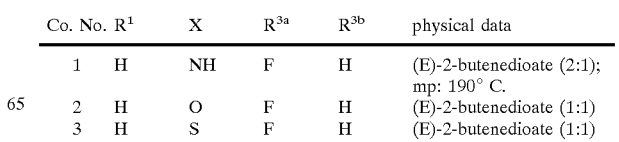

| Co. No. | $R^1$ | X | $R^{3a}$ | $R^{3b}$ | physical data |
|---|---|---|---|---|---|
| 1 | H | NH | F | H | (E)-2-butenedioate (2:1); mp: 190° C. |
| 2 | H | O | F | H | (E)-2-butenedioate (1:1) |
| 3 | H | S | F | H | (E)-2-butenedioate (1:1) |

TABLE 1-continued

[Structure: ketone-linked phenyl with R3a, R3b substituents connected via chain to N in tetrahydropyrido-fused bicycle with X and R1 substituents at positions 6,7]

| Co. No. | R¹ | X | R³ᵃ | R³ᵇ | physical data |
|---|---|---|---|---|---|
| 4 | 7-Cl | NH | F | H | mp. 130° C. |
| 5 | 7-Cl | NH | CH₃ | H | mp. 135° C. |
| 6 | 7-Cl | NH | OCH₃ | OCH₃ | (E)-2-butenedioate (2:1) |
| 7 | 7-Cl | NH | OCH₃ | H | (E)-2-butenedioate (2:1) |
| 8 | 7-Cl | NH | Br | H | (E)-2-butenedioate (1:1); mp. 230° C. |
| 9 | 7-Cl | NH | Cl | H | mp. 154° C. |
| 10 | 6-Cl | S | F | H | hydrochloride (1:1) |
| 11 | 7-OCH₃ | S | F | H | (E)-2-butenedioate (2:1) |
| 12 | 7-Cl | NH | H | H | (E)-2-butenedioate (2:1); mp. 226° C. |
| 13 | 6-CH₃ | S | F | H | (E)-2-butenedioate (1:1) |
| 14 | 6-F | S | F | H | (E)-2-butenedioate (2:1) |
| 24 | H | O | Cl | H | |
| 25 | H | O | OCH₃ | OCH₃ | (E)-2-butenedioate (1:1) |
| 26 | H | O | OCH₃ | H | (E)-2-butenedioate (1:1) |
| 27 | H | N-C₄H₉ | F | H | hydrochloride (1:1) |

TABLE 2

[Structure: similar to Table 1 but with tetrahydro-fused carbocycle (no N in saturated ring)]

| Co. No. | R¹ | X | R³ᵃ | R³ᵇ | physical data |
|---|---|---|---|---|---|
| 15 | H | O | F | H | hydrochloride (1:1) |
| 16 | H | S | F | H | hydrochloride (1:1); mp. 100° C. |
| 17 | H | NH | F | H | — |
| 18 | H | S | CH₃ | H | mp. 75° C. |
| 19 | H | S | H | H | mp. 78° C. |
| 20 | 6-CH₃ | O | F | H | hydrochloride (1:1) |
| 21 | 6-Cl | S | F | H | hydrochloride (1:1) |
| 22 | 6-F | S | F | H | (E)-2-butenedioate (1:1) |
| 23 | 7-OCH₃ | O | F | H | hydrochloride (1:1) |
| 28 | H | NH | F | H | Trans |
| 29 | H | O | OCH₃ | OCH₃ | (E)-2-butenedioate (1:1) |
| 30 | H | O | Cl | H | |
| 31 | H | O | OCH₃ | H | (E)-2-butenedioate (2:1) |
| 32 | 7-Cl | O | F | H | |
| 33 | H | S | Cl | H | |
| 34 | H | S | OCH₃ | H | |

TABLE 3

[Structure: F-substituted benzisoxazole linked via chain to N-containing bicyclic system with X substituent]

| Comp. No. | X | physical data |
|---|---|---|
| 35 | S | (E)-2-butenedioate (2:1) |
| 36 | O | (E)-2-butenedioate (1:1) |
| 37 | NH | (E)-2-butenedioate (2:1) |

C. Pharmacological Examples

Example C1

In vitro Binding Affinity for $\alpha_2$ Receptors

The interaction of the compounds of formula (I) with $\alpha_2$ receptors was assessed in in vitro radioligand binding experiments.

In general, a low concentration of a radioligand with a high binding affinity for a particular receptor is incubated with a sample of a tissue preparation enriched in a particular receptor or with a preparation of cells expressing cloned human receptors in a buffered medium. During the incubation, the radioligand binds to the receptor. When equilibrium of binding is reached, the receptor bound radioactivity is separated from the non-bound radioactivity, and the receptor bound activity is counted. The interaction of the test compounds with the receptor is assessed in competition binding experiments. Various concentrations of the test compound are added to the incubation mixture containing the receptor preparation and the radioligand. Binding of the radioligand will be inhibited by the test compound in proportion to its binding affinity and its concentration.

The radioligand used for $\alpha_{2A}$, $\alpha_{2B}$ and $\alpha_{2C}$ receptor binding is ³H-rauwolscine and the receptor preparation used is the Chinese Hamster Ovary (CHO) cell expressing cloned human $\alpha_{2A}$, $\alpha_{2B}$ and $\alpha_{2C}$ receptors.

The IC₅₀ value (concentration whereby 50% of the receptors is inhibited) for the compounds exemplified in the experimental part above for each of the three receptors ranged between $10^{-6}$ M and $10^{-10}$ M.

Example C2

Dissociation in Receptor Binding Affinity for $\alpha_{2a}$ and Dopamine $D_2$

As already mentioned above, dopamine D2 antagonism may lead to an increased risk of EPS. Thus, the larger the dissociation between $\alpha_{2a}$ and $D_2$, the better. The columns headed "dissociation" show the IC50 value in molar (M) for the $\alpha_{2a}$ receptor and the $D_2$ receptor. By "Ratio" is meant the ratio $D_2/\alpha_a$ and this is an indication for the dissociation between said two receptors.

| Present compounds | dissociation | Art compounds | dissociation |
|---|---|---|---|
| Comp. 1 | $\alpha_{2a}$: 5.0 × 10$^{-9}$<br>$D_2$: 4.0 × 10$^{-7}$<br>Ratio: 79 | Chem. Pharm Bull 1979, 27(8), 1922–6 | $\alpha_{2a}$: 4.1 × 10$^{-8}$<br>$D_2$: 1.0 × 10$^{-7}$<br>Ratio: 2.5 |
| Comp. 2 | $\alpha_{2a}$ 2.6 × 10$^{-10}$<br>$D_2$: 5.0 × 10$^{-7}$<br>Ratio: 1950 | Khim.-Farm Zh. 1975, 9(1), 7–9 | $\alpha_{2a}$: 2.1 × 10$^{-9}$<br>$D_2$: 2.1 × 10$^{-7}$<br>Ratio: 102 |

D. Composition Examples

"Active ingredient" (A.I.) as used throughout these examples relates to a compound of formula (I), a pharmaceutically acceptable addition salt or a stereochemically isomeric form thereof.

Example D1

Capsules 20 g of the A.I., 6 g sodium lauryl sulfate, 56 g starch, 56 g lactose, 0.8 g colloidal silicon dioxide, and 1.2 g magnesium stearate are vigorously stirred together. The resulting mixture is subsequently filled into 1000 suitable hardened gelatin capsules, each comprising 20 mg of the A.I.

Example D2

Film-coated Tablets

Preparation of Tablet Core

A mixture of 100 g of the A.I., 570 g lactose and 200 g starch is mixed well and thereafter humidified with a solution of 5 g sodium dodecyl sulfate and 10 g polyvinyl-pyrrolidone in about 200 ml of water. The wet powder mixture is sieved, dried and sieved again. Then there are added 100 g microcrystalline cellulose and 15 g hydrogenated vegetable oil. The whole is mixed well and compressed into tablets, giving 10.000 tablets, each comprising 10 mg of the active ingredient.

Coating

To a solution of 10g methyl cellulose in 75 ml of denaturated ethanol there is added a solution of 5 g of ethyl cellulose in 150 ml of dichloromethane. Then there are added 75 ml of dichloromethane and 2.5 ml 1,2,3-propanetriol. 10 g of polyethylene glycol is molten and dissolved in 75 ml of dichloromethane. The latter solution is added to the former and then there are added 2.5 g of magnesium octadecanoate, 5 g of polyvinyl-pyrrolidone and 30 ml of concentrated colour suspension and the whole is homogenated. The tablet cores are coated with the thus obtained mixture in a coating apparatus.

What is claimed is:

1. A compound having the formula

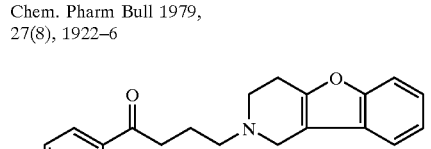

(I)

or a N-oxide form, a pharmaceutically acceptable addition salt or a stereochemically isomeric form thereof, wherein:

Alk is $C_{5-12}$alkanediyl;

n is 1 or 2;

p is 1 and q is 2; or p is 2 and q is 1;

X is —O—, —S—, or NH;

each $R^1$ is independently hydrogen, halogen, $C_{1-6}$alkyl, nitro, hydroxy or $C_{1-4}$alkyloxy;

D is a radical of formula

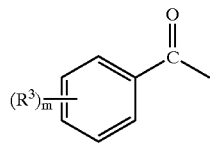

(a)

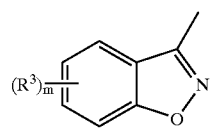

(b)

wherein m is 1 or 2; and each $R^3$ independently is hydrogen, $C_{1-4}$alkyl, $C_{1-4}$alkyloxy or halo.

2. A compound according to claim 1 wherein n is 1 and $R^1$ is hydrogen, chloro, fluoro, methyl, methoxy or nitro.

3. A compound according to claim 1 wherein Alk is 1,5-pentanediyl.

4. A method for treating depression or Parkinson's disease in a patient, comprising administering a therapeutically effective amount of a compound according to claim 1 to a patient in need thereof.

5. A composition comprising a pharmaceutically acceptable carrier and, as active ingredient, a therapeutically effective amount of a compound as claimed in claim 1.

6. A process for preparing a composition according to claim 5 comprising combining said compound as the active ingredient in admixture with a pharmaceutically acceptable carrier.

7. A process for preparing a compound of formula (I) according to claim 1, comprising, a) N-alkylating an intermediate of formula (II) with an alkylating reagent of formula (III)

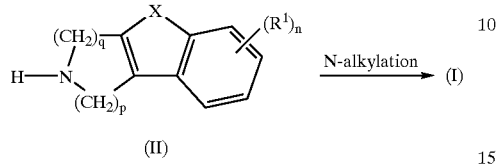

wherein $W^1$ is a leaving group, in a reaction-inert solvent, in the presence of a base and optionally in the presence of a catalyst;

b) and optionally, interconverting a first compound of formula I to yield a second compound of formula I, and further, optionally, converting the compounds of formula (I), into a therapeutically active non-toxic acid addition salt by treatment with an acid, or into a therapeutically active non-toxic base addition salt by treatment with a base, or converting the acid addition salt form into the free base by treatment with alkali, or converting the base addition salt into the free acid by treatment with acid; and, optionally, preparing stereochemically isomeric forms or N-oxides thereof.

* * * * *

UNITED STATES PATENT AND TRADEMARK OFFICE
CERTIFICATE OF CORRECTION

PATENT NO. : 6,576,640 B1  Page 1 of 1
DATED : June 10, 2003
INVENTOR(S) : Kennis et al.

It is certified that error appears in the above-identified patent and that said Letters Patent is hereby corrected as shown below:

Column 16,
Line 66, delete "$a_a$" and insert therefor -- $a_{2a}$ --.

Signed and Sealed this

Twentieth Day of January, 2004

JON W. DUDAS
*Acting Director of the United States Patent and Trademark Office*

UNITED STATES PATENT AND TRADEMARK OFFICE
CERTIFICATE OF CORRECTION

PATENT NO. : 6,576,640 B1
DATED : June 10, 2003
INVENTOR(S) : Kennis et al.

It is certified that error appears in the above-identified patent and that said Letters Patent is hereby corrected as shown below:

Column 4,
Line 19, delete "4methylbenzenesulfonyloxy" and insert therefor
-- 4- methylbenzenesulfonyloxy --.

Column 9,
Lines 53-58, please delete the two paragraphs in their entirety and insert therefor the following paragraph:

--The present invention thus also relates to compounds of formula (I) as defined hereinabove for use as a medicine. Further, the present invention also relates to the use of a compound of formula (I) for the manufacture of a medicament for treating depression or Parkinson's disease.--

Column 11,
Line 42, after "$CH_2Cl_2$" insert -- / --.
Line 46, delete "$HCl_2$/2-propanol" and insert therefor -- HCl/2-propanol --.
Line 47, delete "temprature" and insert therefor -- temperature --.

Column 12,
Line 47, delete "$HCl_2$/2-propanol" and insert therefor -- HCl/2-propanol --.

Column 13,
Line 21, delete "$HCl_2$/2-propanol" and insert therefor -- HCl/2-propanol --.

Column 14,
Line 28, delete "farctions" and insert therefor -- fractions --.

Column 15,
Lines 40-45, please insert -- N -- where shown in the following formula:

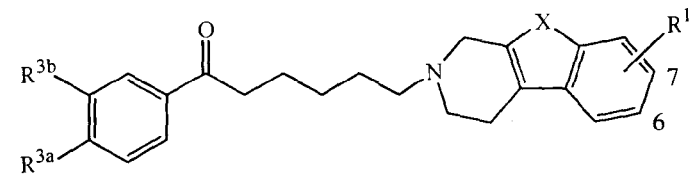

UNITED STATES PATENT AND TRADEMARK OFFICE
CERTIFICATE OF CORRECTION

PATENT NO. : 6,576,640 B1
DATED : June 10, 2003
INVENTOR(S) : Kennis et al.

It is certified that error appears in the above-identified patent and that said Letters Patent is hereby corrected as shown below:

Column 16,
Line 66, delete "$a_a$" and insert therefor -- $a_{2a}$ --.

This certificate supersedes Certificate of Correction issued January 20, 2004.

Signed and Sealed this

Twelfth Day of October, 2004

JON W. DUDAS
*Director of the United States Patent and Trademark Office*